US008950026B2

(12) United States Patent
Valdemoros Tobia et al.

(10) Patent No.: US 8,950,026 B2
(45) Date of Patent: Feb. 10, 2015

(54) INTELLIGENT HOSPITAL BED AND METHOD FOR OPERATING SAME

(75) Inventors: Oscar Valdemoros Tobia, Logroño (ES); Manuel Chica Serrano, Jaen (ES); Ruben Rodriguez Velazquez, Santander (ES); Christopher Thorpe, Farnham (GB); Loftus Hall, London (GB); Ewa Lada, Nowa Iwiczna (PL); Bernard Vaucher, Neuchatel (CH); Roberto Gueli, Catania (IT); Erhard Giese, Flensburg (DE); Adelino Figueiredo Da Silva, Travanca (PT)

(73) Assignees: Industrias Tobia, S.A., Logrono (ES); Lincis-Solucoes Integradas Para Sistemas de Informacao, Lda, Braga (PT); Fos Messtechnik GmbH, Schacht-audorf (DE)

( * ) Notice: Subject to any disclaimer, the term of this patent is extended or adjusted under 35 U.S.C. 154(b) by 128 days.

(21) Appl. No.: 13/698,491

(22) PCT Filed: May 18, 2010

(86) PCT No.: PCT/ES2010/070332
§ 371 (c)(1),
(2), (4) Date: Feb. 27, 2013

(87) PCT Pub. No.: WO2011/144767
PCT Pub. Date: Nov. 24, 2011

(65) Prior Publication Data
US 2013/0152308 A1    Jun. 20, 2013

(51) Int. Cl.
*A47B 7/02* (2006.01)
*A61G 7/012* (2006.01)
(Continued)

(52) U.S. Cl.
CPC . *A61G 7/012* (2013.01); *A61B 5/11* (2013.01); *A61B 5/447* (2013.01); *A61B 5/6892* (2013.01); *A61G 7/008* (2013.01); *A61G 7/015* (2013.01); *A61G 7/018* (2013.01); *A61G 2203/32* (2013.01)
USPC ...................................... 5/618; 5/610; 5/613

(58) Field of Classification Search
CPC ....... A61G 7/012; A61G 7/005; A61G 7/008; A61G 7/018; A61G 7/00
USPC ............................. 5/607–611, 613, 616–618
See application file for complete search history.

(56) References Cited

U.S. PATENT DOCUMENTS 3,267,493 A * 8/1966 Pruim et al. .................... 5/611
4,084,274 A    4/1978 Willis et al.
(Continued)

FOREIGN PATENT DOCUMENTS

DE    100 09 314 A1    9/2001
EP    1 486 191 A1    12/2004
(Continued)

*Primary Examiner* — Robert G Santos
*Assistant Examiner* — Myles Throop
(74) *Attorney, Agent, or Firm* — Birch, Stewart, Kolasch & Birch, LLP

(57) ABSTRACT

The invention relates to an intelligent hospital bed comprising a lower main frame (1) and an upper frame (2) articulated to said lower main frame provided with movable parts, in which there is arranged a mattress (22) provided with several foldable sections, including a plurality of sensors arranged along the mattress (22) capable of measuring the initial force on the point at which the corresponding sensor is arranged, which sensors are interconnected to one another and associated with a control unit which controls servo-motors used for moving the movable parts of the upper frame (2) such that when a sensor detects a movement of the user in real time, a servo-motor which is associated with a corresponding sensor or a combination of sensors (S) moving at least one of the movable parts of the upper frame (2) is actuated.

14 Claims, 10 Drawing Sheets

(51) Int. Cl.
*A61B 5/11* (2006.01)
*A61B 5/00* (2006.01)
*A61G 7/008* (2006.01)
*A61G 7/015* (2006.01)
*A61G 7/018* (2006.01)

(56) References Cited

U.S. PATENT DOCUMENTS

| | | | |
|---|---|---|---|
| 4,658,450 A | 4/1987 | Thompson | |
| 5,010,772 A | 4/1991 | Bourland et al. | |
| 5,479,665 A | 1/1996 | Cassidy et al. | |
| 5,502,853 A * | 4/1996 | Singleton et al. | 5/609 |
| 5,592,705 A * | 1/1997 | West | 5/424 |
| 6,105,187 A * | 8/2000 | Gnjatovic | 5/618 |
| 6,386,051 B1 * | 5/2002 | Yoshimi et al. | 73/862.046 |
| 7,246,389 B2 * | 7/2007 | Taguchi et al. | 5/618 |
| 8,672,842 B2 * | 3/2014 | Kenalty et al. | 600/300 |
| 2004/0148704 A1 | 8/2004 | Tekulve | |
| 2005/0160530 A1 * | 7/2005 | Taguchi et al. | 5/618 |
| 2005/0251914 A1 | 11/2005 | Schaller et al. | |
| 2007/0163045 A1 * | 7/2007 | Becker et al. | 5/616 |
| 2008/0172789 A1 * | 7/2008 | Elliot et al. | 5/616 |
| 2009/0013469 A1 * | 1/2009 | Johnson | 5/612 |
| 2009/0237264 A1 * | 9/2009 | Bobey et al. | 340/815.69 |
| 2010/0069795 A1 | 3/2010 | Kang et al. | |
| 2014/0022081 A1 * | 1/2014 | Ribble et al. | 340/573.4 |

FOREIGN PATENT DOCUMENTS

| | | |
|---|---|---|
| ES | 8800592 A1 | 2/1988 |
| GB | 2 313 540 A | 12/1997 |
| GB | 2 369 047 A | 5/2002 |
| JP | 2001-293037 A | 10/2001 |
| WO | WO 2004/021952 A2 | 3/2004 |
| WO | WO 2008/065402 A1 | 6/2008 |

* cited by examiner

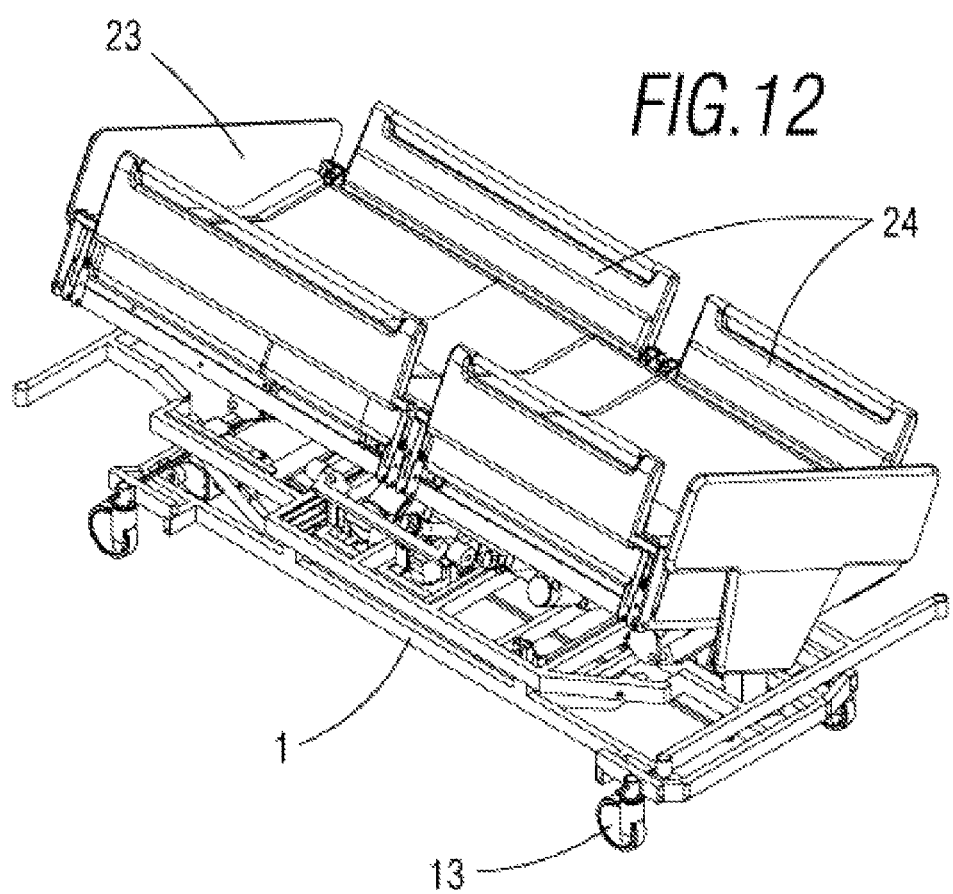

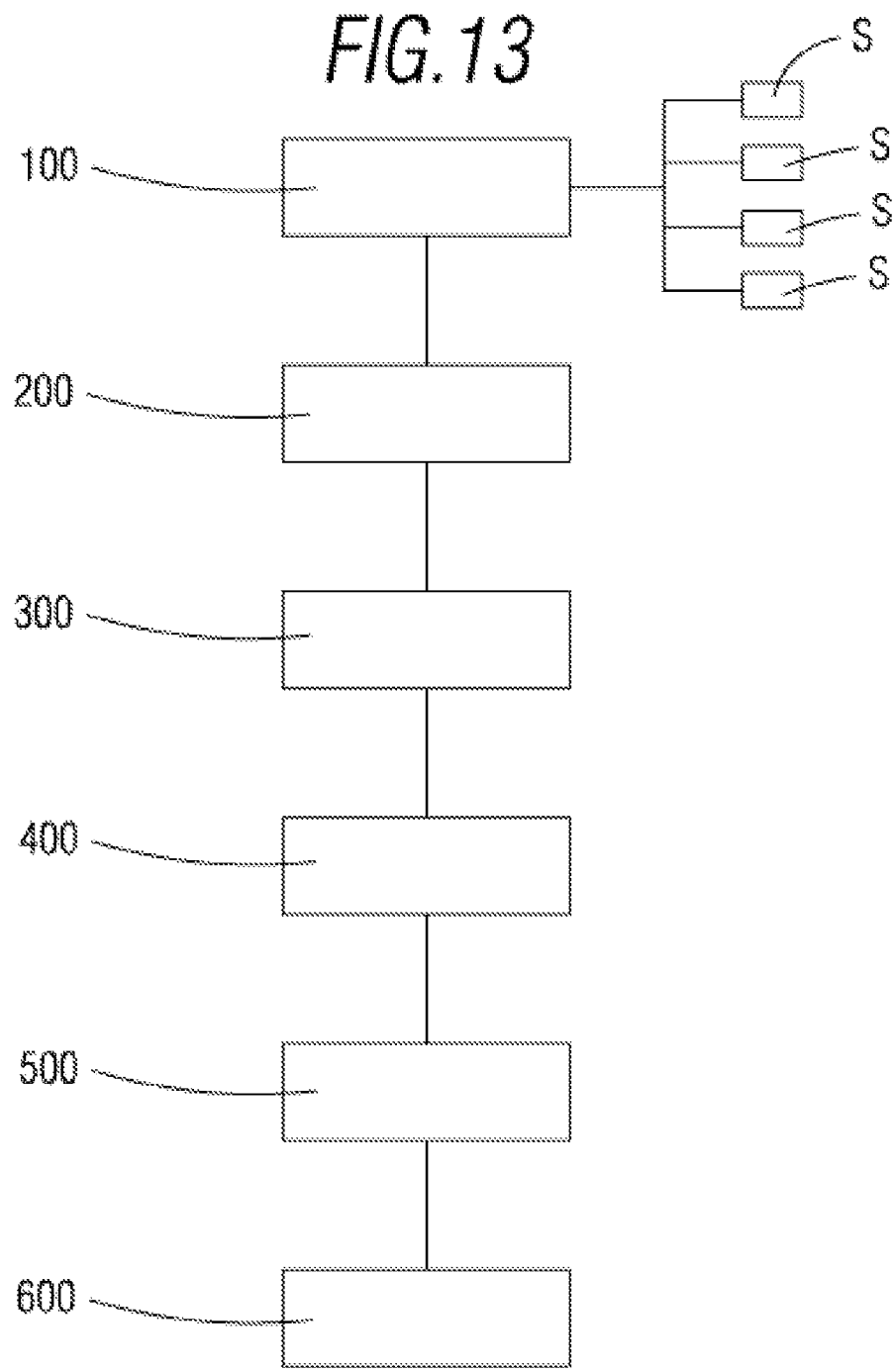

INTELLIGENT HOSPITAL BED AND METHOD FOR OPERATING SAME

OBJECT OF THE INVENTION

The present invention patent application is aimed at the registration of an intelligent hospital bed and a method for operating same incorporating remarkable innovations and advantages.

More specifically, the invention proposes the development of an interactive hospital bed which allows improving the quality of life both of the patient lying on the bed and of the healthcare personnel as it detects the movements of the patient lying on the bed.

BACKGROUND OF THE INVENTION

Positioning patients with reduced mobility on beds in health care centers is of great importance to prevent impairing health and to improve comfort during treatment.

The lack of autonomy to perform basic movements and posture changes may cause distress and discomfort in a patient which could negatively influence his/her health.

A wide variety of beds provided with a mechanism which can be electrically actuated allowing performing certain movements in an automated manner, such as raising-lowering or inclining a horizontal section of the bed itself, being actuated by means of a push button or remote control system which can be actuated by the user him/herself or by healthcare personnel in the case of a patient with reduced mobility, is known today.

However, despite the advantages of such electric beds, nurses must manually change the position of the patient every 2 or 4 hours according to the situation of the patient, for example, for drug administration, cleaning, etc. Constant and prolonged manual handling of patients by healthcare personnel can cause back pains in the latter that may result in a sick leave with the subsequent economic losses. Furthermore, another equally significant drawback is that in all the known actuation mechanisms there is always a need for actuation by the patient him/herself or healthcare personnel using push buttons, such that there is a need to find a system or device providing the patient with a higher degree of autonomy when moving the bed.

DESCRIPTION OF THE INVENTION

The present invention has been developed for the purpose of providing a hospital bed solving the aforementioned drawbacks, further providing other additional advantages which will be evident from the description attached below.

Therefore, an object of the present invention is to provide an intelligent hospital bed of the type comprising a lower main frame 1 and an upper frame 2 articulated to the lower main frame 1 provided with movable parts, in which there is arranged a mattress 22 provided with several foldable sections. More particularly, the bed is characterized in that it includes a plurality of sensors arranged along the mattress 22 capable of measuring the initial force on the point at which the corresponding sensor is arranged. These sensors, connected by means of a data multiplexing system to minimize internal wiring, are associated with a control unit which controls servo-motors used for moving the movable parts of the upper frame 2, such that when a sensor detects a movement of the user in real time, a servo-motor associated with a corresponding sensor moving one of the movable parts of the upper frame 2 is actuated. Such sensors generate complete pressure images of the patient which are analyzed in real time by means of specific intelligent software based on automatic learning and image processing techniques for the purpose of interpreting the patient's intentions from very small movements. The software thus decides whether the patient wants to sit up, lean back, turn over onto one side or the other or stay in the current position as a result of analyzing the evolution of the characteristics of the patient extracted from the information provided by the sensors.

In this specification, a servo-motor is understood as an assembly formed by an electric motor and a piston-cylinder which can be actuated by the electric motor.

Therefore, the objective of the invention is to design a specialized hospital bed with a functionality from the functional point allowing patients with reduced mobility to change their position on the bed without needing the intervention of hospital personnel, providing greater comfort for the patient or due to the needs of the treatment that must be received by the patient on account of his/her disease. One actuation system will change the bed configuration with respect to the side and seated positions of the patient, several positions having been provided.

A support system based on an intelligent detection system which allows interpreting the movement of the patient and activating the system of motors has been proposed as a result. Another equally significant advantage is that it prevents the need of having remote controls and provides more autonomy to the patient since the bed can move without needing healthcare personnel.

This hospital bed is especially useful for elderly patients who may have greater movement limitations.

Pressure sensors preferably comprise the plurality of sensors.

In order for the patient (or user) to get out of bed in a considerably upright position, at one end of the bed there is provided at least one bar 16 articulated on one side to the lower main frame 1 and at the other end to the lower assembly 3 of the upper frame 2 which can follow an angular trajectory, whereas at an opposite end of the bed there is provided at least one bar 17 which is articulated at one end to the lower main frame 1 and has at its opposite end wheels 18 which can slide on guides 19 located in the lower assembly 3 of the upper frame 2. These two bars 16, 17 can be actuated by means of servo-motors 20, 21.

Advantageously, the lower assembly 3 includes a raising/lowering mechanism articulated to a central support part 6 of the upper assembly 4 which allows moving of the central support part 6, and therefore the mattress 22, linearly up/down, raising/lowering mechanism 8 being controlled by a servo-motor.

According to another aspect of the present invention, the aforementioned raising/lowering mechanism 8 can have a rectangular framework provided with two sets of wheels, each of the sets being in opposite crosspieces 37 of the rectangular framework, which wheels are placed on guide rails located transversely with respect to the longitudinal axis of the lower assembly 3. The central support part 6 can thus move transversely with respect to the longitudinal plane of the bed.

Furthermore and advantageously, the aforementioned upper assembly 4 of the bed can be articulated to the lower main frame 1 by means of a servo-motor, such that it allows tilting of the lower assembly with respect to the longitudinal axis of the lower main frame 1 in both directions.

Another object of the present invention is to provide a method for operating a hospital bed such as that described above which comprises the steps of:

obtaining a map of pressure images from the data obtained by each sensor;

segmenting the pressure images;

calculating the characteristics of each of the image segments;

obtaining a relative difference of each of the characteristics of the patient with respect to the map of pressure images; and recognizing the patient's intention to move in real time actuating one or more actuators causing the movement of at least one movable part of the frame.

Other features and advantages of the bed object of the present invention will be evident from the description of a non-exclusive preferred embodiment illustrated by way of non-limiting example in the attached drawings, in which:

BRIEF DESCRIPTION OF THE DRAWINGS

FIG. 12 is a rear perspective view of the position depicted in FIG. 10; and

FIG. 13 is a block diagram depicting the method for operating the bed of the invention in order to move it.

DESCRIPTION OF A PREFERRED EMBODIMENT

Figure 1:
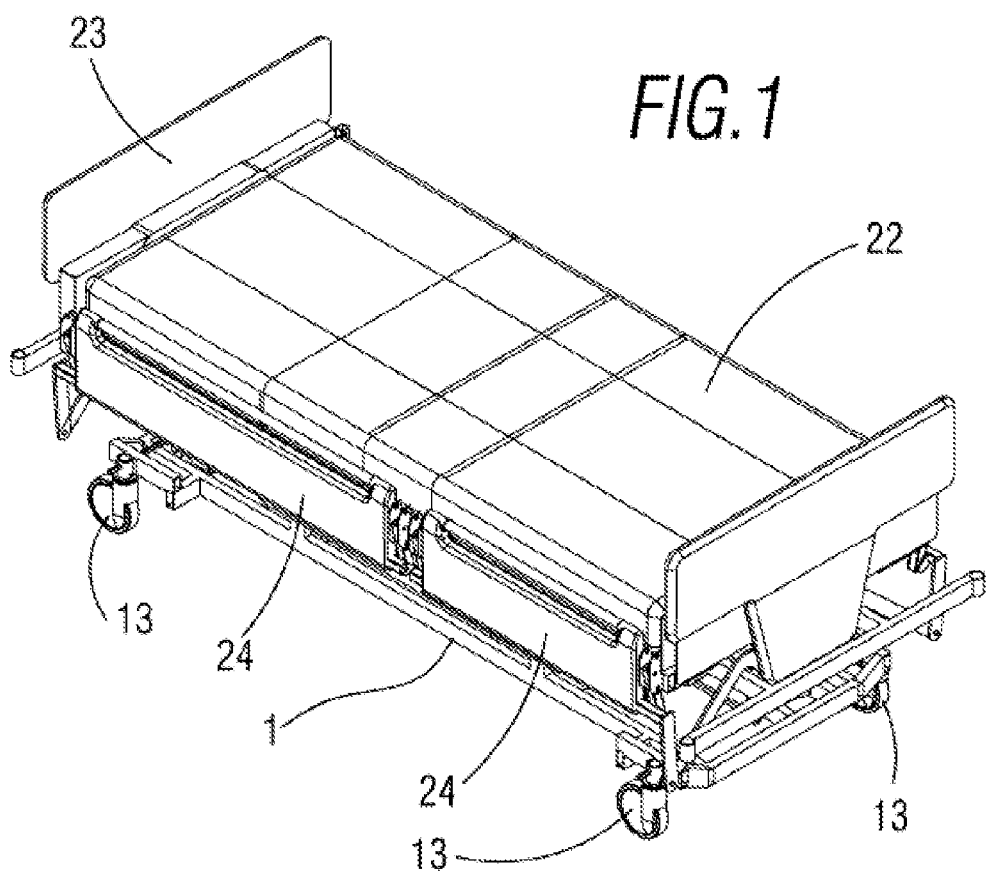
FIG. 1 is a perspective view of a hospital bed according to the present invention in a resting condition with the mattress completely extended horizontally.

As shown in the attached drawings, an embodiment of the intelligent hospital bed according to the invention essentially comprises a lower main frame 1 formed by a metal structure with a rectangular base, and an upper frame 2 articulated to the lower main frame 1 provided with movable parts which are described in greater detail below, in which a mattress 22 provided with a plurality of foldable sections is arranged on top. In this description, mattress 22 is understood as both a single deformable body and as several independent portions with different sizes which define a mattress 22 with a rectangular base in a planar and horizontal position.

This hospital bed which is described in greater detail below is suitable for patients with reduced mobility because it allows adopting different positions, such as lying face up in a horizontal position, on a side, seated, lying face down and in an inclined position in an automated manner and without needing healthcare personnel to be attentive to the needs of the patient at all times.

The lower assembly of the upper frame 2 is formed by a metal structure, and is articulated to the lower main frame 1 at two pivot points 32 located at opposite lateral sides which allow the inclination thereof at two points opposite one another, and an upper assembly 4 on which the mattress 22 rests. This upper assembly 4 is provided with three longitudinal support parts 5, 6 and 7, the two support parts 5, 7 corresponding to the lateral ends being articulated to the central support part 6 such that they can be inclined integrally at the same time in different positions, as can be seen in the different drawings.

For the purpose of facilitating patient mobility without external help, i.e., of healthcare personnel, there is provided a plurality of interconnected sensors (not depicted) arranged along the mattress 22 capable of measuring the initial force on the point at which the corresponding sensor is arranged, which sensors are associated with a control unit (actuating means) which controls servo-motors located at different points of the hospital bed used for moving the movable parts of the upper frame 2. Therefore, when one or more sensors detects a specific movement of the user in real time, a servo-motor associated with a corresponding sensor or sensors moving at least one of the many movable parts of the mentioned upper frame 2 is actuated. These sensors have been distributed in the mattress 22 at specific points corresponding with the most important parts of the patient's body, centers of mass or pressure distributions.

The information generated by the preceding sensors is used by software linked to the control unit (actuating means) for moving the different actuators provided in the bed, thus creating a simpler and more intuitive interface with the patient.

Therefore the method for operating the bed described herein has the steps of:

obtaining a map of pressure images 100 from the data obtained by each sensor S arranged in the mattress 22;

segmenting 200 the pressure images;

calculating 300 the characteristics of each of the image segments;

obtaining a relative difference 400 of each of the characteristics of the patient with respect to the map of pressure images; and recognizing 500 the patient's intention to move in real time actuating one or more actuators causing the movement 600 of at least one movable part of the frame of the bed being adapted to the patient's needs.

Referring again to each of the support parts 5, 6 and 7, it comprises a fixed portion 5A, 6A and 7A on which there are pivotally articulated inclinable portions 5B-5C, 6B-6C and 7B-7C which are linked to the foldable sections of the mattress 22, the articulation point having a pin 25. One of the inclinable portions 5B, 6B and 7B is designed for supporting the back of the user forming a type of backrest, while the other articulated sections are designed for supporting the lower limbs of the user.

As can be seen, the fixed portion 5A, 6A and 7A of the longitudinal support parts 5, 6 and 7 comprises a structure defined by two stringers 33 attached by means of transverse end crosspieces 34, the transverse end crosspieces 34 including inclined flanges 14 which are provided with through holes 35 through which pins 38 acting as a rotating shaft are inserted. The central support part 6, more specifically the fixed part 6A, has a servo-motor 15 articulated to inclinable portion 6B which allows inclining inclinable portion 6B with respect to the fixed portion 6A. To move the three inclinable portions 5B, 6B and 7B simultaneously when actuating the servo-motor 15, fixing elements 26 are arranged in the upper part of the inclinable portions 5B, 6B and 7B. A servo-motor 27 (see FIG. 4) articulated to inclinable portion 6C, which allows inclining of inclinable portion 6C with respect to the fixed portion 6A, is also provided.

Figure 10:
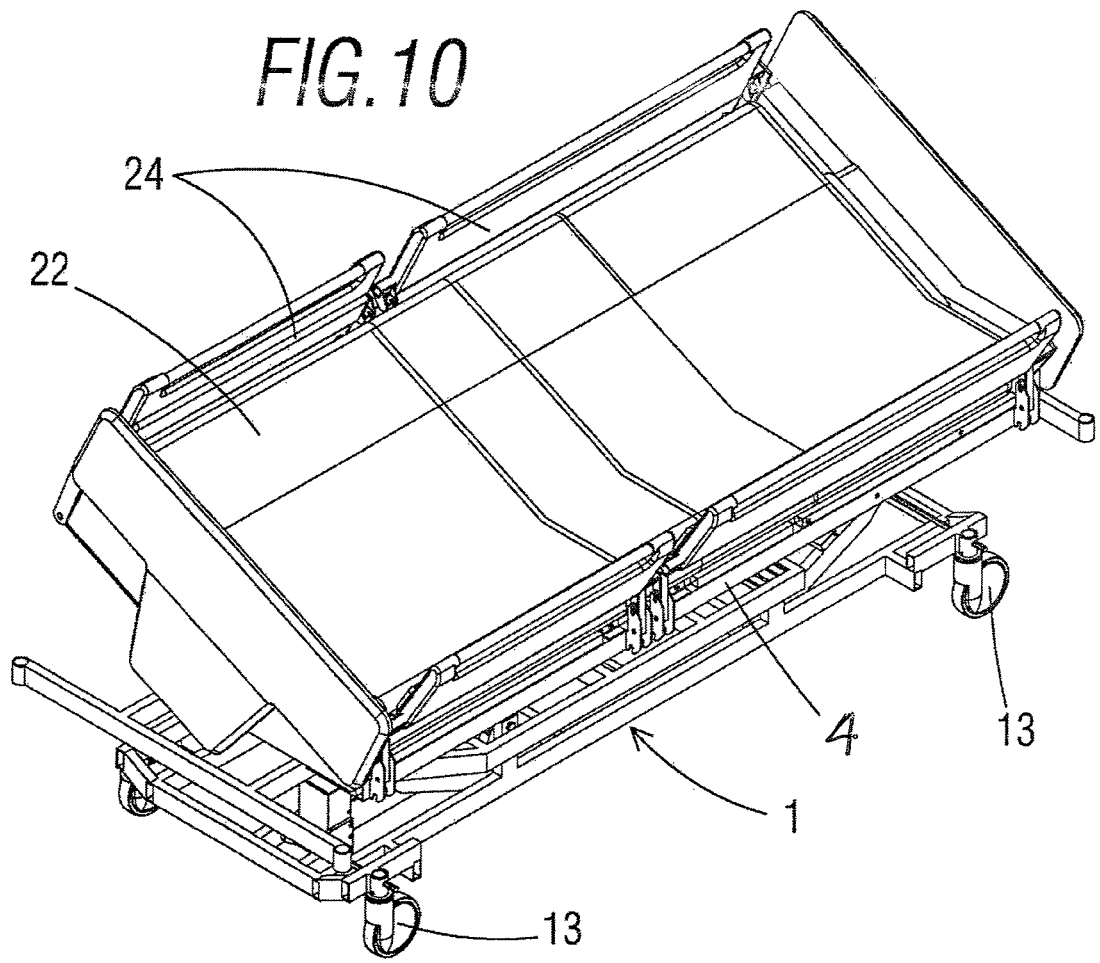
FIG. 10 is a front perspective view of the hospital bed in which the sections of the mattress are folded together.
Figure 11:
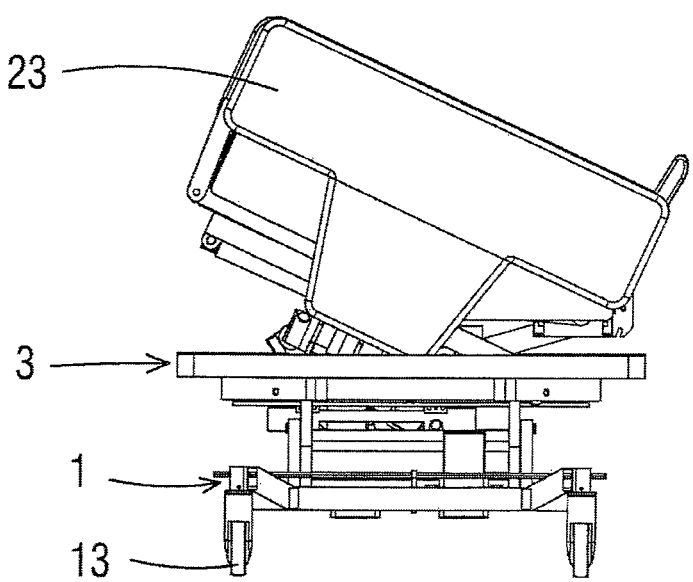
FIG. 11 is a side elevational view of the position depicted in FIG. 10.

FIGS. 10-12 show how the upper assembly 4 is in a tilted position with respect to the central longitudinal axis of the bed and where one of the support parts 7 also has a different degree of inclination with respect to the other two support parts 5 and 6 as a result of the presence of the articulation points defined by flanges 14 and of the arrangement of two servo-motors 29, 30 located in the part lower of the central support part 6, one of the servo-motors 29 being associated with support part 5 whereas the other servo-motor 30 is associated with support part 7. To that end, projecting tabs 31 have been arranged on one of the sides of the respective support parts 5 and 7 (see FIG. 4) which are fixed to the corresponding servo-motor by means of pins 38. As a result, the patient using the bed of the invention can adopt a larger number of positions with respect to the known art.

Figure 4:
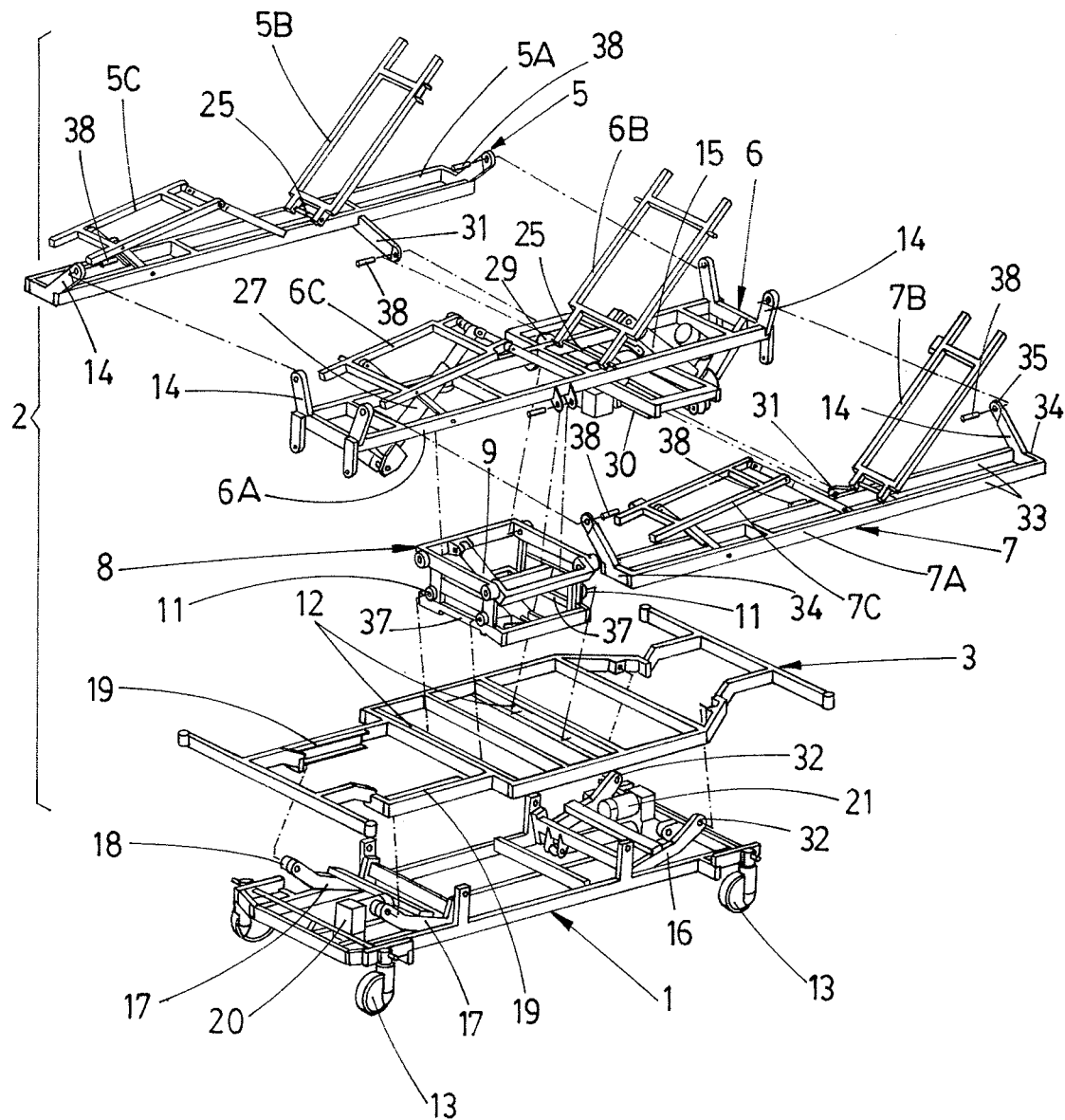
FIG. 4 is an exploded perspective view of the hospital bed of the invention where the main parts are shown.
Figure 5:
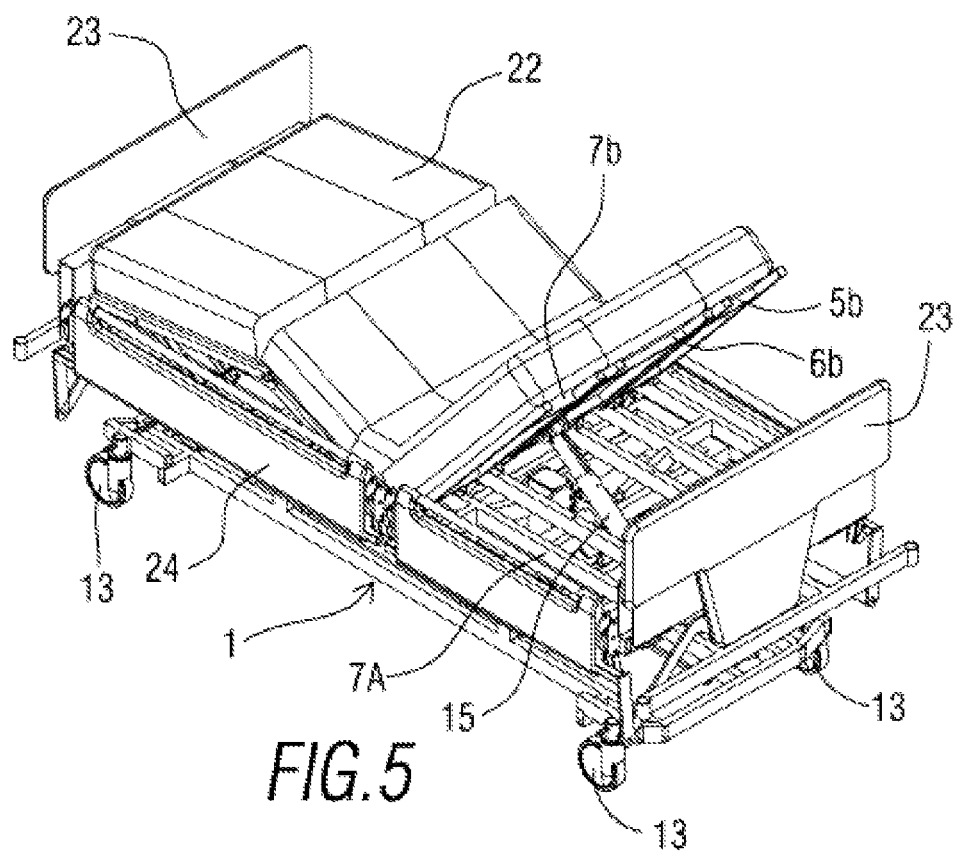
FIG. 5 is a perspective view of the bed with the different sections forming the mattress adopting different planes simultaneously.
Figure 6:
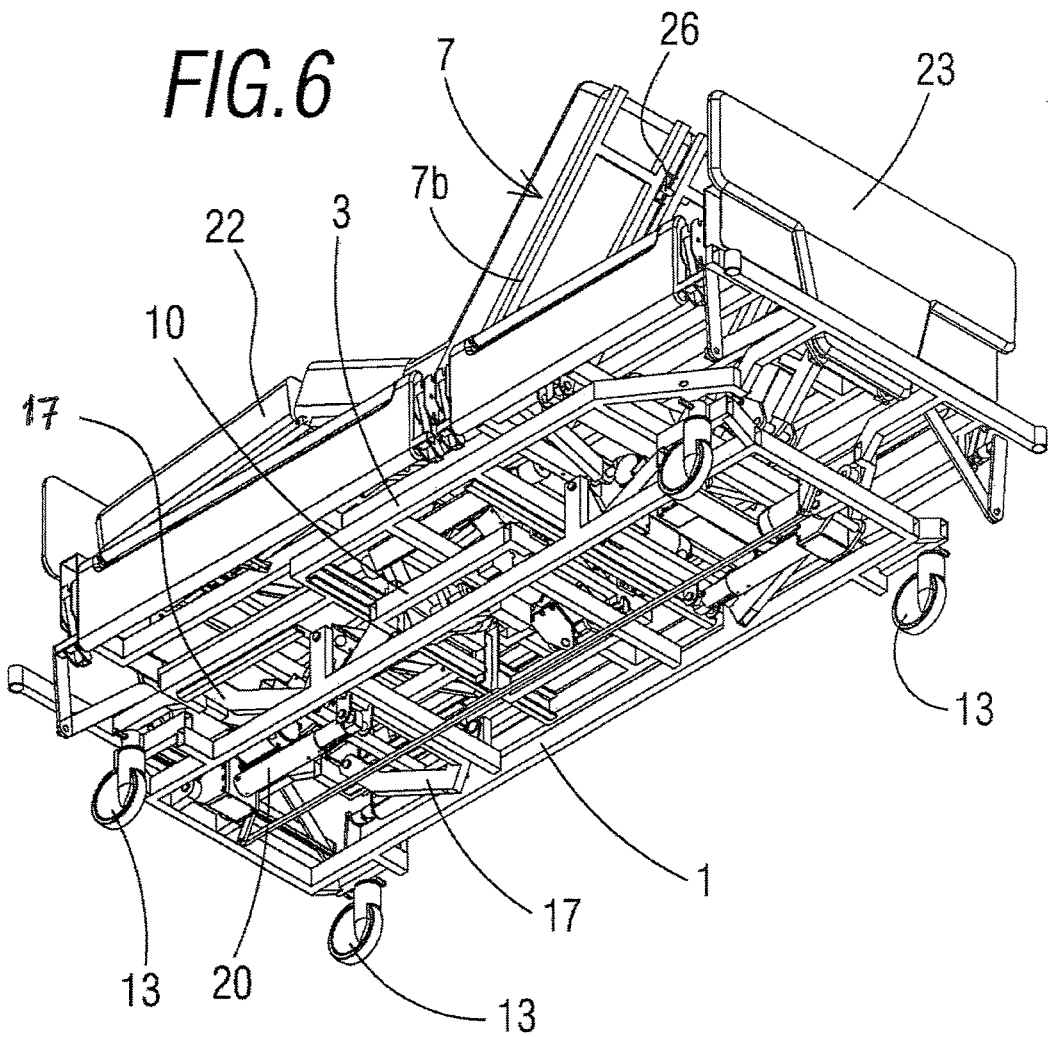
FIG. 6 is a perspective view of the hospital bed as seen from the bottom.

Additionally, as seen more clearly in FIG. 4, the lower assembly 3 includes a raising/lowering mechanism 8, which is articulated to the central support part 6 of the upper assembly 4, which allows moving central support part 6 linearly up/down, the raising/lowering mechanism 8 being controlled by a servo-motor 9. This raising/lowering mechanism 8 comprises a rectangular framework 10 provided with two sets of wheels 11, the sets of wheels 11 being in opposite crosspieces 37 of the rectangular framework 10, which wheels 11 are placed on guide rails 12 (formed by channel irons) located transversely with respect to the longitudinal axis of the lower assembly 3, such that the central support part 6 can move transversely with respect to the longitudinal plane of the hospital bed.

Furthermore, at one end there is provided a pair of bars 16 parallel to one another, which are articulated to the lower main frame 1 and the lower assembly 3 of the upper frame which can follow an angular trajectory, whereas at an opposite end there is provided a pair of bars 17 articulated at one end to the lower main frame 1 and has at its opposite end wheels 18 which can slide on guides 19 located in the lower assembly 3 of the upper frame 2 longitudinally.

Figure 2:
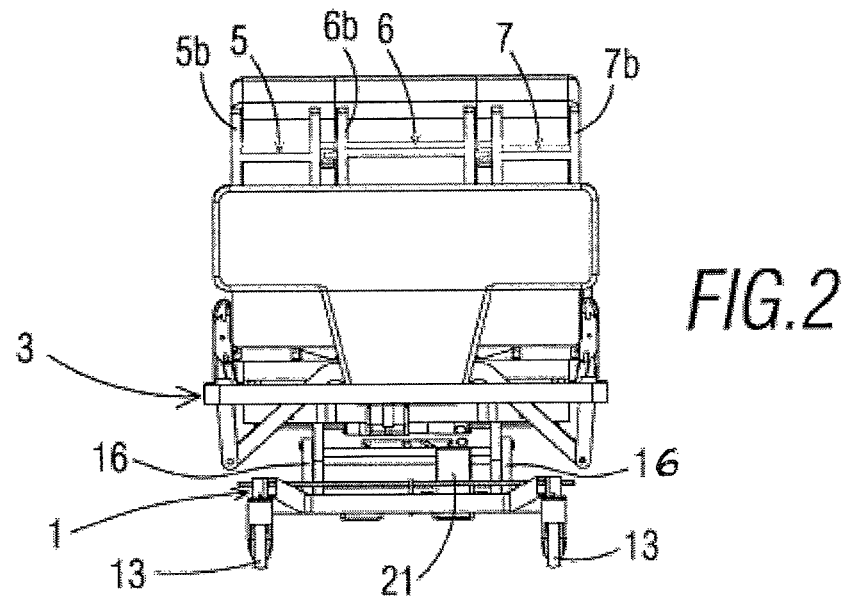
FIG. 2 is a front elevational view of the hospital bed.
Figure 3:
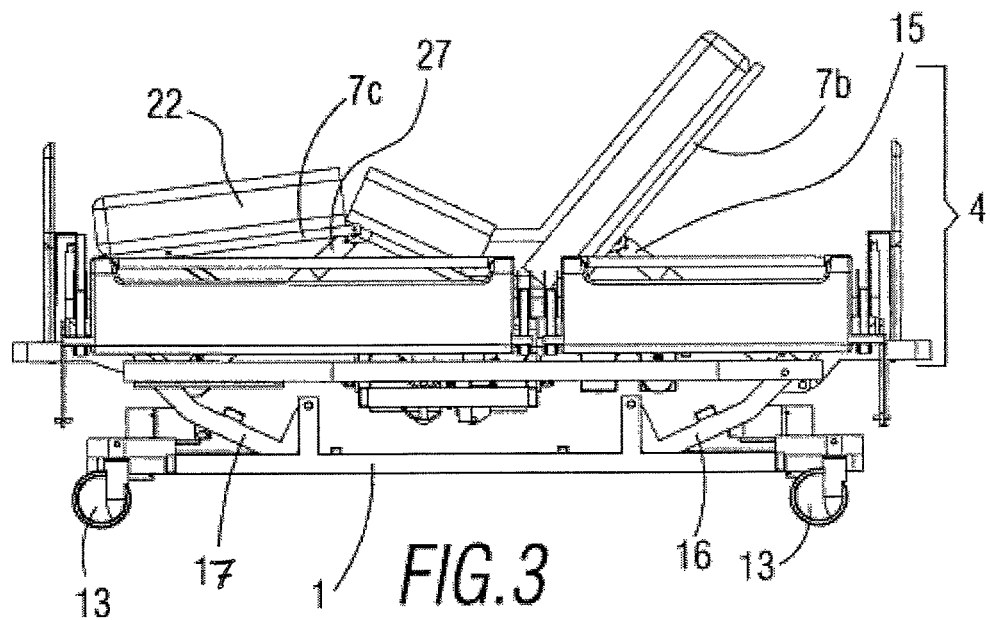
FIG. 3 is a side elevational view of the hospital bed with the different sections forming the mattress in different planes.
Figure 7:
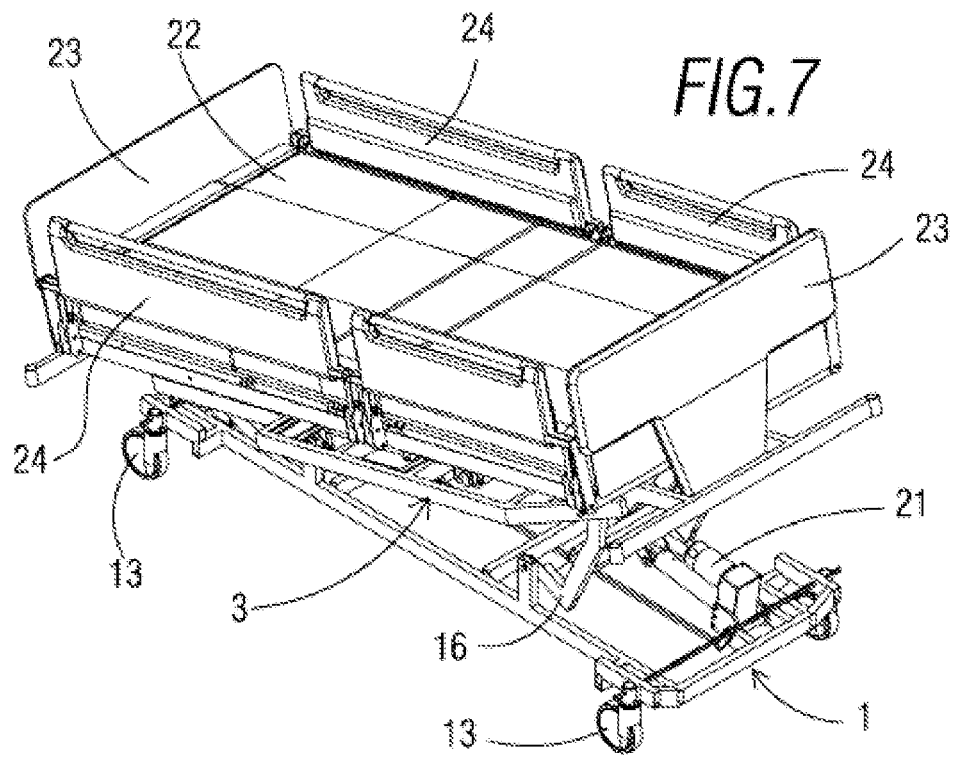
FIG. 7 is a perspective view of the bed of the present invention with the upper frame pivoted from one of its ends.
Figure 8:
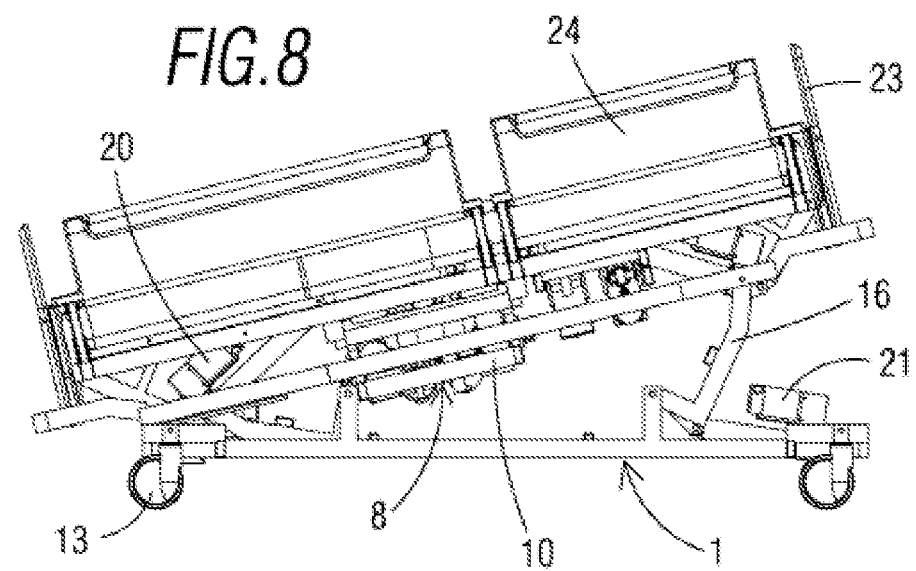
FIG. 8 is a side elevational view of the bed depicted in FIG. 7 with the upper frame pivoted from one of its ends.

The bars 16, 17 are actuated by a corresponding servo-motor 20, 21 which act when the sensors send a signal to the control unit First bars 16 are shown in FIGS. 2, 7 and 8, and the second bars 17 are shown in FIGS. 3 and 4.

The lower main frame 1 is provided with four swivel caster wheels 13 located in each of the corners which allow moving the hospital bed in any direction.

The hospital bed described herein can optionally have a remote control (not depicted) as an additional control and safety element which also allows for the different movements of the movable parts of the hospital bed even though it is not necessary for operating the bed when the patient is lying down.

Plates 23 located in the front and rear part of the hospital bed as well as retractable side railings 24 preventing the patient from being able to fall off while lying thereon are also arranged, such side railings 24 being shown for example in a not-in-use condition in FIG. 1, whereas the side railings 24 are raised in FIGS. 7 and 8.

Figure 9:
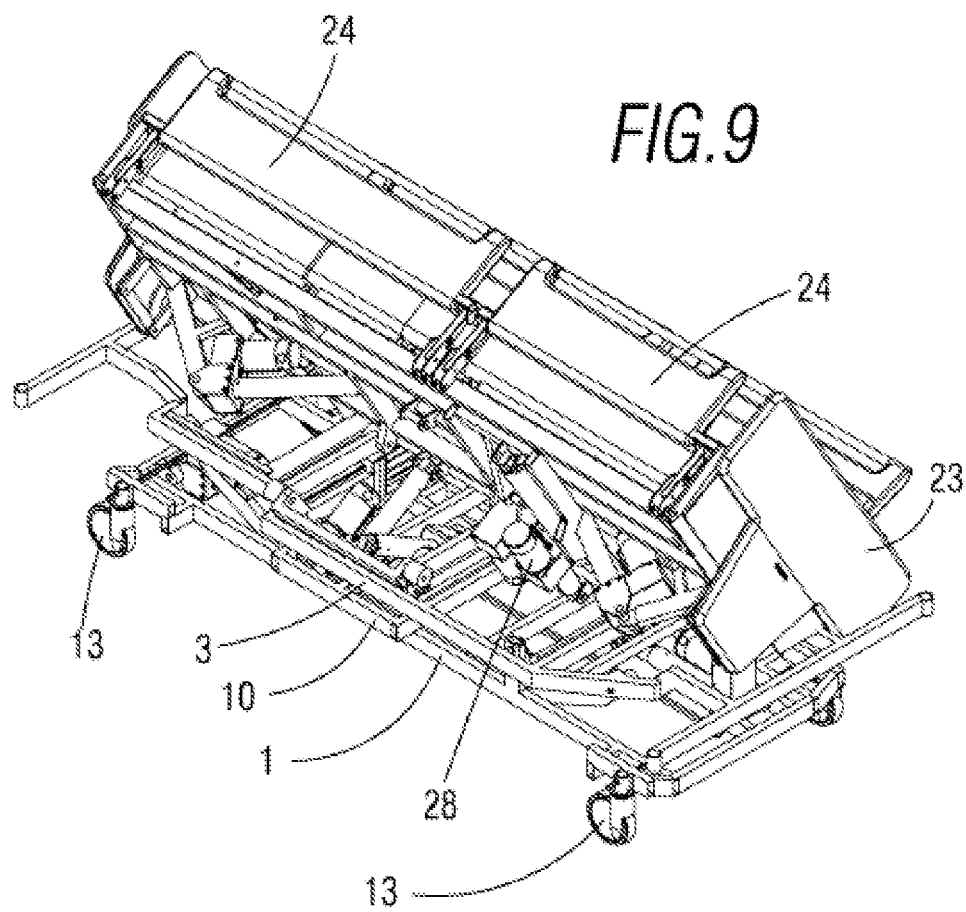
FIG. 9 is a perspective view of a second embodiment of the hospital bed with the upper frame tilted with respect to the longitudinal axis of the bed.

As can be seen starting from FIG. 9, in an alternative embodiment of the invention, there is a possibility that the upper assembly 4 is articulated to the lower main frame 1 by means of a servo-motor 28 which also allows tilting of the upper assembly 4 with respect to the longitudinal axis thereof in both directions (right and left).

It must be pointed out that the same reference numbers have been used in the second embodiment to define common elements or parts provided in the two embodiments described herein.

Details, shapes, dimensions and other accessory elements, as well as the materials used in manufacturing the bed of the invention may be conveniently replaced with others which are technically equivalent and do not depart from the essential nature of the invention nor the scope defined by the claims included below.

The invention claimed is:

1. An intelligent hospital bed comprising:
a lower main frame,
an upper frame provided with movable parts and articulated to the lower main frame, and
a mattress provided with several foldable sections on which a patient rests, the mattress including a plurality of pressure sensors arranged along the mattress capable of measuring the initial force of the patient at a point at which the corresponding sensor is arranged,
wherein the upper frame includes multiple moving parts including:
a lower assembly articulated to the lower main frame in at least two pivot points located at opposite ends of the lower main frame; and
an upper assembly on which the mattress rests, the upper assembly being provided with a right side longitudinal support part, a left side longitudinal support part, and a central support part which are connected to each other, the left and right side longitudinal support parts being connected to and respectively articulated to left and right lateral ends of the central support part, such that each of the support parts is capable of being inclined,
the lower assembly including a raising/lowering mechanism articulated to the central support part of the upper assembly,
wherein the pressure sensors are interconnected and associated with a control unit which controls multiple servo-motors adapted to move the movable parts of the upper frame, such that, when one or more of the pressure sensors detects a movement of the patient in real time, the control unit creates a map of pressure images to be processed to actuate specific servo-motors associated with the one or more of the pressure sensors for moving at least one of the movable parts of the upper frame; and
wherein the raising/lowering mechanism is adapted to be controlled by another of the servo-motors in order to control a linear up and down movement of the central support part,
wherein each of the right side support part, the left side support part, and the central support part of the upper frame includes:
a fixed portion and an inclinable portion pivotally articulated to the fixed portion,
the inclinable portions of the right side support part, the left side support part, and the central support part being linked to foldable sections of the mattress, wherein the intelligent hospital bed is configured to automatically recognize a pattern indicating and intention of the patient to sit up, lean back, or turn over from the map of pressure images, and to cause a movement of at least one of the movable parts of the upper frame in real time by action of the servo motors.

2. The hospital bed according to claim 1, further comprising:

at least one first bar provided at a head end of the bed, which is capable of being actuated by one of servo-motors at the head end of the bed, the at least one first bar being articulated to the lower main frame and to the lower assembly of the upper frame, so that the upper frame follows an angular trajectory, at least one second bar provided at a foot end of the bed, which is capable of being actuated by one of the servo-motors at the foot end of the bed, the at least one second bar having one end articulated to the lower main frame and having a wheel on an opposite end thereof, the wheel being capable of sliding on a guide located in the lower assembly of the upper frame.

3. The hospital bed according to claim 2, wherein the servo-motor at the head end of the bed and the servo-motor at the foot end of the bed are operable independently from one another.

4. The hospital bed according to claim 1, wherein the raising/lowering mechanism includes a substantially square framework provided with two sets of wheels, each of the sets of wheels being in one of two crosspieces extending transversely across front and rear sides of the framework,
wherein the wheels of the raising/lowering mechanism are placed on guide rails located transversely with respect to a longitudinal axis of the lower assembly.

5. The hospital bed according to claim 1, wherein the lower main frame is provided with caster wheels.

6. The hospital bed according to claim 1, wherein the upper assembly is articulated to the lower main frame, and
one or more of the servo-motors are provided which are capable of tilting the upper assembly in left and right directions with respect to a longitudinal axis of the lower main frame.

7. The hospital bed according to claim 1, wherein each of several portions of the mattress is provided with at least one of the sensors.

8. The hospital bed according to claim 1, wherein each of the lateral ends of the central support part articulated respectively to the right and left side support parts is provided with one of the servo-motors, such that each of the right and left side support parts is able to adopt a different inclination with respect to the central support part.

9. A method for operating the hospital bed according to claim 1, comprising a plurality of pressure sensors arranged on the mattress on the upper frame provided with the movable parts, the movable parts being moved in real time by the specific servo-motors, comprising the steps of:
obtaining a map of the pressure images from data obtained by each of the sensors which are treated by the control unit controlling the movable parts;
forming pressure images in multiple segments;
calculating discriminating statistical characteristics of each of the segments of the images;
obtaining a relative difference of each of the characteristics of the patient resting on the bed with respect to the map of the pressure images for quantifying a pressure evolution of the patient.

10. An intelligent hospital bed comprising:
a lower main frame,
an upper frame provided with movable parts and articulated to the lower main frame, and
a mattress provided with several foldable sections on which a patient rests, the mattress including a plurality of pressure sensors arranged along the mattress capable of measuring the initial force of the patient at a point at which the corresponding sensor is arranged, wherein the upper frame includes multiple moving parts including:
a lower assembly articulated to the lower main frame in at least two pivot points located at opposite ends of the lower main frame; and
an upper assembly on which the mattress rests, the upper assembly being provided with a right side longitudinal support part, a left side longitudinal support part, and a central support part which are connected to each other, the left and right side longitudinal support parts being connected to and respectively articulated to left and right lateral ends of the central support part, such that each of the support parts is capable of being inclined,
the lower assembly including a raising/lowering mechanism articulated to the central support part of the upper assembly,
wherein the pressure sensors are interconnected and associated with a control unit which controls multiple servo-motors adapted to move the movable parts of the upper frame, such that, when one or more of the pressure sensors detects a movement of the patient in real time, the control unit creates a map of pressure images to be processed to actuate specific servo-motors associated with the one or more of the pressure sensors for moving at least one of the movable parts of the upper frame; and
wherein the raising/lowering mechanism is adapted to be controlled by another of the servo-motors in order to control a linear up and down movement of the central support part, and
wherein a fixed portion of each of the longitudinal support parts includes a structure defined by two stringers attached by transversely extending crosspieces, the transversely extending crosspieces at opposite ends of the bed including flanges provided with through holes through which pins, acting as rotating shafts, are inserted, wherein the intelligent hospital bed is configured to automatically recognize a pattern indicating and intention of the patient to sit up, lean back, or turn over from the map of pressure images, and to cause a movement of at least one of the movable parts of the upper frame in real time by action of the servo motors.

11. The hospital bed according to claim 10, wherein at least one of the right side and left side longitudinal support parts is associated with one or more of the servo-motors.

12. The hospital bed according to claim 10, wherein each of the right side support part, the left side support part, and the central support part of the upper frame includes:
a fixed portion and an inclinable portion pivotally articulated to the fixed portion,
the inclinable portions of the right side support part, the left side support part, and the central support part being linked to foldable sections of the mattress.

13. The hospital bed according to claim 12, wherein each of the lateral ends of the central support part articulated respectively to the right and left side support parts is provided with one of the servo-motors, such that each of the right and left side support parts is able to adopt a different inclination with respect to the central support part.

14. The hospital bed according to claim 10, wherein the raising/lowering mechanism includes a substantially square framework provided with two sets of wheels, each of the sets of wheels being in one of two crosspieces extending transversely across front and rear sides of the framework,
wherein the wheels of the raising/lowering mechanism are placed on guide rails located transversely with respect to a longitudinal axis of the lower assembly.

* * * * *